(12) United States Patent
Nieuwenhuis et al.

(10) Patent No.: US 9,575,081 B2
(45) Date of Patent: *Feb. 21, 2017

(54) DEVICE AND METHODS FOR DETECTING ANALYTES IN SALIVA

(71) Applicants: Jeroen Hans Nieuwenhuis, Eindhoven (NL); Ahmed Mohammed Taki Jehanli, Abingdon (GB); Femke Karina De Theije, Eindhoven (NL); Eduard Gerard Marie Pelssers, Eindhoven (NL)

(72) Inventors: Jeroen Hans Nieuwenhuis, Eindhoven (NL); Ahmed Mohammed Taki Jehanli, Abingdon (GB); Femke Karina De Theije, Eindhoven (NL); Eduard Gerard Marie Pelssers, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 80 days.

This patent is subject to a terminal disclaimer.

(21) Appl. No.: 14/191,043

(22) Filed: Feb. 26, 2014

(65) Prior Publication Data

US 2014/0179024 A1    Jun. 26, 2014

Related U.S. Application Data

(63) Continuation of application No. 12/993,100, filed as application No. PCT/IB2009/052196 on May 26, 2009, now Pat. No. 9,103,843.

(30) Foreign Application Priority Data

May 27, 2008   (EP) .................................... 08156984

(51) Int. Cl.
   *G01N 33/94*     (2006.01)
   *B01L 3/00*      (2006.01)
   (Continued)

(52) U.S. Cl.
   CPC ..... *G01N 33/9486* (2013.01); *B01L 3/502753* (2013.01); *G01N 27/745* (2013.01);
   (Continued)

(58) Field of Classification Search
   CPC .............. G01N 33/9486; G01N 27/745; G01N 33/54326; G01N 33/54393; G01N 33/946
   See application file for complete search history.

(56) References Cited

U.S. PATENT DOCUMENTS 4,336,173 A    6/1982 Ugelstad
4,459,378 A    7/1984 Ugelstad
(Continued)

FOREIGN PATENT DOCUMENTS

CN    1646909 A1    7/2005
EP    0174704 A2    3/1986
(Continued)

OTHER PUBLICATIONS

Wang, R. et al "Patterning Hydroxyapatite Biocoating by Electrophoretic Deposition" Journal of Biomedical Materials Research, Part A, Oct. 1, 2003, vol. 67, No. 1, pp. 270-275.
(Continued)

*Primary Examiner* — Melanie Y Brown

(57) ABSTRACT

The invention provides a device for detecting drugs of abuse or other compounds in saliva. The invention thus provides a device for detecting the presence of one or more analytes in a saliva sample, comprising: (a) One or more pre-treatment regions for specifically or non-specifically removing at least a part of the fraction of the saliva sample interfering with detection of the one or more analytes; and (b) A detection
(Continued)

region comprising a biosensor surface, the surface comprising: molecules capable of specifically binding the one or more analytes; or the one or more analytes and/or analyte analogues.

14 Claims, 4 Drawing Sheets

(51) Int. Cl.
  *G01N 27/74* (2006.01)
  *G01N 33/543* (2006.01)
(52) U.S. Cl.
  CPC . *G01N 33/54326* (2013.01); *G01N 33/54393* (2013.01); *G01N 33/946* (2013.01)

(56) References Cited

U.S. PATENT DOCUMENTS

| | | | |
|---|---|---|---|
| 4,654,267 A | 3/1987 | Ugelstad | |
| 5,143,752 A | 9/1992 | Nakajima | |
| 5,308,580 A * | 5/1994 | Clark | B01L 3/502 422/419 |
| 5,981,297 A | 11/1999 | Baselt | |
| 6,838,005 B2 | 1/2005 | Tepper | |
| 2002/0106377 A1 | 8/2002 | Tsang | |
| 2003/0162304 A1 | 8/2003 | Dority | |
| 2005/0124077 A1 | 6/2005 | Cole | |
| 2005/0164404 A1 | 7/2005 | Sloane et al. | |
| 2006/0036206 A1 | 2/2006 | Yokoyama et al. | |
| 2006/0183170 A1 * | 8/2006 | Tachino | G01N 33/56944 435/7.32 |
| 2006/0292035 A1 | 12/2006 | Gould et al. | |
| 2007/0031283 A1 | 2/2007 | Davis | |
| 2008/0207556 A1 * | 8/2008 | Nick | A61K 31/522 514/44 R |
| 2008/0311002 A1 * | 12/2008 | Kirby | B01L 3/5023 422/68.1 |

FOREIGN PATENT DOCUMENTS

| | | |
|---|---|---|
| EP | 1020726 A1 | 7/2000 |
| JP | 62-212317 A | 9/1987 |
| JP | 2003-287529 A | 10/2003 |
| JP | 2008-105953 A | 5/2008 |
| WO | 9526503 A1 | 10/1995 |
| WO | 0169258 A1 | 9/2001 |
| WO | 0198765 A1 | 12/2001 |
| WO | 02082040 A1 | 10/2002 |
| WO | 03005037 A1 | 6/2003 |
| WO | 2004046693 A1 | 6/2004 |

OTHER PUBLICATIONS

Amerongen et al., Interaction of human salivary muclns with hydroxyapatite. J Biol Buccale. Jun. 1989;17(2.

* cited by examiner

DEVICE AND METHODS FOR DETECTING ANALYTES IN SALIVA

CROSS-REFERENCES TO RELATED APPLICATIONS

This application is a continuation of prior U.S. patent application Ser. No. 12/993,100, filed Nov. 17, 2010, which was the National Stage of International Application No. PCT/IB2009/052196, filed May 26, 2009, which claims the benefit of European Patent Application (EPO) No. 08156984.0, filed May 27, 2008, the entire contents of each of which is incorporated herein by reference thereto.

FIELD OF THE INVENTION

The present invention relates to devices and methods for detecting and/or quantifying molecules in a saliva sample. The methods and devices combine pre-treatment and detection.

BACKGROUND OF THE INVENTION

In a diagnostic test one or more specific target molecules or analytes have to be measured. Often this is done by allowing the target molecule to interaction in a (bio-chemical) reaction, which directly or indirectly results in a detectable signal.

SUMMARY OF THE INVENTION

A number of devices and methods are currently commercially available to perform road-side testing of drugs. Most of these are based on immunological detection of the target, which is performed on the sample directly in WO 02/082040, a "one-device" system is described for determining different analytes, in particular drugs, in body fluids. The bodily fluid is collected via a collection end of the device with an absorbent pad, a series of pressure heads inside the cap of the collection device forces the sample (as the collection end of the device passes through the pressure heads) into the core of an immunoassay system containing diagnostic strips for drug detection. The drug in the sample competes with a drug conjugate immobilized on a membrane support for limited antibody sites on colored microspheres. A colored line indicates the presence or absence of the relevant drugs in the sample. A portion of the sample is retained in a confirmation sample retention well, which is sealed from the outside and stored for further testing.

Many of these tests have however been demonstrated to be unsatisfactory, primarily with respect to the sensitivity of the assays. This is in part caused by the fact that the concentration of most drugs in saliva is usually somewhat lower than in blood or urine. More importantly however, saliva contains components which interfere with many detection methods. Although saliva is largely composed of water, it additionally contains many different substances. These include electrolytes (e.g. sodium, potassium, calcium, magnesium, chloride, bicarbonate, phosphate), antibacterial compounds (such as thyocyanate, hydrogen peroxide, immunoglobulin A), enzymes (e.g. amylases, lysozymes, lipases, phosphatases, amidases, dehydrogenases, peroxidases, superoxide dismutase, transferases, isomerases), cells (both bacterial cells and host cells, i.e. of the animal or human producing the saliva), and other compounds such as hormones. Most importantly however, saliva contains mucus, consisting mainly of mucopolysaccharides and glycoproteins.

An important class of glycoproteins found in saliva are the mucins. These are a family of large, heavily glycosylated proteins. At least 19 human mucin genes have been distinguished by cDNA cloning—MUC1, 2, 3A, 3B, 4, SAC, 5B, 6-9, 11-13, and 15-19. Mucins are secreted as massive aggregates of proteins with molecular masses of roughly 0.1 to 10 million Da. Within these aggregates, monomers are linked to one another mostly by non-covalent interactions, although intermolecular disulfide bonds may also play a role in this process. Mucins have been demonstrated to be responsible for most of the false positive testing of saliva samples.

In order to accurately determine the presence of drugs in saliva, prior extraction of the analytes or removal of interfering components (such as mucins) is required. Typically, solid phase clean-up systems are used for removing interfering compounds or isolating the analyte of interest by binding to the stationary phase. The unbound compounds are washed away and out of the column. Where the analyte is bound to the column, it is thereafter eluted using an appropriate buffer capable of dislodging the adsorbed analyte from the stationary phase. Alternatively, where the interfering compound is bound, the eluate containing the analyte is collected directly. The eluate is optionally evaporated and re-dissolved in a smaller volume to pre-concentrate it prior to analysis using methods such as, but not limited to, enzyme-linked immunosorbent assay (ELISA), radio immunoassay (MA), high performance liquid chromatography (HPLC), liquid chromatography mass spectrometry (LC-MS) and gas chromatography mass spectrometry (GC-MS).

The traditional analytical methods have several disadvantages however. First, these methods are time-consuming and expensive. Moreover they often require complex instruments and a relatively high degree of skill on the part of the person performing the analysis.

Accordingly, there is a need for testing devices and methods which allow accurate and sensitive detection of analytes in saliva without requiring extensive equipment or highly trained technicians.

The present invention provides devices and methods whereby pre-treatment of the sample and detection are performed subsequently in the same setting, offering ease of manipulation as well as high specificity and sensitivity. These methods and devices are of particular use in the testing of analytes in saliva. Moreover, the methods and devices allow use outside a laboratory environment.

The integration of a pre-treatment region and a detection region in one device offers several advantages. There is less need for user intervention with the sample. As a consequence, there is less chance of errors introduced by sample manipulation. Also, less sample material is required. Indeed, there is no loss of sample as is the case when transferring sample material from one device to another. Moreover, this ensures minimal contact of the user with the sample material, minimizing risk of contamination of the sample.

The methods and devices of the present invention envisage a pretreatment of the sample prior to detection, whereby components interfering with detection are removed. This allows the use of magnetizable particles in the device without affecting sensitivity or specificity. Indeed, the interfering fraction which typically induces aggregation of magnetizable particles is removed prior to contacting with the magnetizable particles. This results in a reduction of the background signal or aspecific binding reduced. Moreover the methods and devices of the present invention allow for detection based on magnetic actuation. This is of particular importance as magnetic actuation can be used to further speed up the diagnostic tests and simplify fluidics in e.g. a microfluidic device. Accordingly the methods and devices described in the present invention provide rapid, sensitive, and robust tools for determining analytes in saliva.

Devices and methods described herein are also particularly suitable for use in indirect detection methods, i.e. methods wherein unbound analyte or analyte-specific reagent is detected as a measure for the presence and optionally amount of analyte in a sample, such as e.g. a competition assay.

The devices and methods of the present invention can be used for tests which require a minimum of handling, especially outside laboratory environments (e.g. roadside testing, point of care tests). Consequently, the devices may be provided as devices for single use, or as cartridges in a microfluidics device.

Accordingly, present invention provides devices for detecting the presence of one or more analytes in a saliva sample, comprising:
(a) one or more pre-treatment regions for specifically or non-specifically removing at least a part of the fraction of the saliva sample interfering with detection of the one or more analytes; and
(b) a detection region comprising a biosensor surface, the surface comprising:
molecules capable of specifically binding the one or more analytes; or
the one or more analytes and/or analyte analogues.

According to particular embodiments, devices are provided which are microfluidic devices. According to alternative particular embodiments, devices are provided which are lateral flow devices.

According to a particular embodiment, devices are provided wherein one or more pre-treatment regions are comprised in one or more separate chambers containing magnetizable particles coated with a molecule capable of specifically or aspecifically binding to components in the saliva sample interfering with detection of the one or more analytes. In particular, these magnetizable particles are paramagnetic or superparamagnetic particles.

In alternative embodiments, devices are provided with one or more pre-treatment regions comprising a surface which comprises a molecule capable of specifically or non-specifically binding to components in the saliva sample interfering with detection of the one or more analytes. The molecule binding to components in the saliva sample may be bound to the surface, or the surface may largely or essentially consist of such molecule. The former is typically the case when molecules capable of specifically binding are envisaged; the latter is envisaged when molecules non-specifically binding to components in the saliva sample are used. However, this is only a general rule and should not be interpreted as limiting this embodiment.

According to further specific embodiments, devices are provided comprising a surface which comprises a molecule capable of specifically or non-specifically binding to components in the saliva sample interfering with detection of the one or more analytes, which surface is porous. According to yet further specific embodiments, the porous surface is a sintered porous structure.

According to particular embodiments devices are provided comprising a molecule binding to components in the saliva sample interfering with detection of the one or more analytes, which is hydroxyapatite.

According to particular embodiments, devices are provided comprising a molecule specifically binding to components in the saliva sample interfering with detection of the one or more analytes, which molecule is an antibody. According to further particular embodiments, the antibody is an antibody against an aggregation factor. According to most particular embodiments, the antibody is an anti-mucin antibody.

According to specific embodiments devices are provided which comprise an intermediary region for containing the saliva sample prior to contacting the sample with the detection region. This intermediary region may simply be for transporting the sample (e.g. a channel, such as a microfluidics channel in a microfluidics device; or an inert region in a lateral flow device). However, the intermediary region may also have another function, such as contacting the sample with one or more reagents prior to contacting the sample with the detection region.

According to particular embodiments, devices are provided wherein the detection region or the intermediary region of the device is a separate chamber containing magnetizable particles coated with a molecule capable of specifically binding the one or more analytes, which is different from the molecule on the biosensor surface.

According to particular embodiments devices are provided suitable for single use.

Methods using devices such as those described herein are also envisaged. According to a particular embodiments methods are provided for detecting the presence of one or more analytes in a saliva sample, comprising the steps of contacting the saliva sample with a device, the devise comprising:
(a) One or more pre-treatment regions for specifically or non-specifically removing at least a part of the fraction of the saliva sample interfering with detection of the one or more analytes; and
(b) A detection region comprising a biosensor surface, the surface comprising:
molecules capable of specifically binding the one or more analytes; or
the one or more analytes and/or analyte analogues
which methods comprise detecting the presence of the analyte in the detection region in a competitive or non-competitive assay.

According to particular embodiments, methods are provided which comprise a step of incubating the saliva sample with magnetizable particles coated with a molecule capable of specifically or a-specifically binding to components in the saliva sample interfering with detection of the one or more analytes, in at least one of the one or more pre-treatment regions.

According to particular embodiments methods are provided wherein the molecule binding to components in the saliva sample interfering with detection of the one or more analytes is hydroxyapatite.

According to alternative particular embodiments, methods are provided wherein the molecule binding to components in the saliva sample interfering with detection of the one or more analytes is an antibody. According to further particular embodiments, the antibody is an antibody against an aggregation factor. According to most particular embodiments, the antibody is an anti-mucin antibody.

According to specific embodiments methods are provided comprising the step of contacting a sample with the one or more pre-treatment regions and thereafter the step of contacting the sample with the detection region, and whereby after contacting with the pre-treatment region(s), the sample is contacted with magnetizable particles coated with a molecule capable of specifically binding the one or more analytes, which is different from the molecule on the biosensor surface.

According to particular embodiments, methods are provided for use in drug detection, in particular drug of abuse detection. Thus, according to these embodiments, at least one of the analytes to be detected is a drug.

Another aspect of the invention relates to the benefits of the filtering of saliva over hydroxyapatite. Thus, methods for detecting one or more analytes in a saliva sample are provided which comprise contacting the saliva sample with hydroxyapatite prior to performing detection of the analyte(s).

BRIEF DESCRIPTION OF THE DRAWINGS

The above and other characteristics, features and advantages of the present invention will become apparent from the following detailed description, taken in conjunction with the accompanying Figures, which illustrate, by way of example, the principles of the invention. This description is given for the sake of example only, without limiting the scope of the invention. The reference Figures quoted below refer to the attached drawings.

DETAILED DESCRIPTION OF THE EMBODIMENTS

Figure 1:
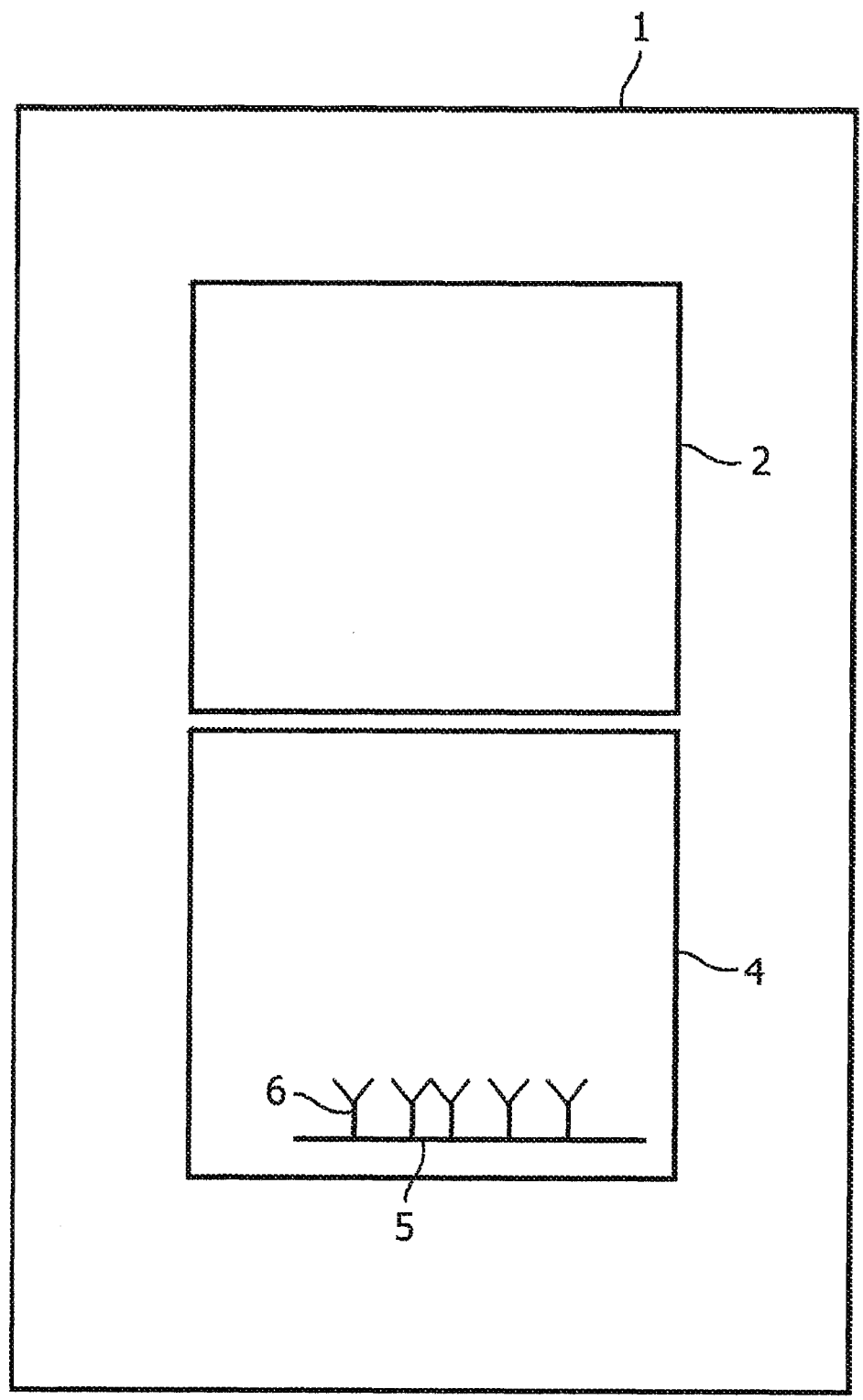
FIG. 1 shows a schematic representation of a device (1) according to a particular embodiment of the invention, comprising a pre-treatment region (2) and detection region (4). The detection region (4) comprises a biosensor surface (5) which comprises, in this embodiment, molecules (6) capable of specifically binding the one or more analytes.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The terms or definitions used herein are provided solely to aid in the understanding of the invention.

DEFINITIONS

The term "analyte" as used herein refers to a compound in a sample of which the detection of presence and/or concentration is desired.

The term "analyte-analogue" as used herein refers to a molecule which is similar to the analyte in that it binds analyte-specific probes. However, analyte-analogues bind more weakly to analyte specific probes than the analyte, such that the binding of the analyte-analogue with a probe can be displaced by the presence of the analyte. Analyte analogue as used herein for example refers to a molecule used in e.g. a competition assay. In this type of assay, only one analyte binding molecule (typically an antibody) is used. The analyte analogue is a compound which is structurally different but nevertheless structurally related to the analyte and is equally bound by the analyte binding molecule.

In a such a competition assay, both analyte and analyte analogue will compete for binding to the same analyte binding molecule. Herein the analyte analogue binding molecule binds with the same affinity, or with a lower affinity for the analyte binding molecule than the analyte itself, such that the analyte-analogue bound to the analyte binding molecule can be displaced by the analyte. Typically an analyte analogue shares a same epitope with an analyte for an analyte binding antibody. Reasons for using an analyte analogue, instead of the analyte itself in such a competition assay, are for example its ease in synthesis, ease in coupling to a substrate, enhanced stability and/or shelf life, or lowered risks in the manufacture of a test device such as lowered toxicity or lower pharmaceutical activity than the analyte itself (e.g. bacterial toxins, drugs of abuse).

The phrase "detecting the presence" as used herein refers to the qualitative and/or quantitative detection of the presence of an analyte. Detecting the presence also encompasses detecting the absence of the analyte, i.e. the finding that no detectable analyte is present. Similarly, the quantitative detection of an analyte encompasses the detection of the absence of the analyte, corresponding to a zero level as well as detection of quantifiable levels of analyte.

The term "pre-treatment", as used herein, refers to a manipulation (typically a purification) performed on a sample prior to detection with the aim of optimizing detection. Such pre-treatment can involve removal of molecules from the sample, based either on physical (e.g. size, viscosity) or biochemical properties of these molecules (e.g. specific or non-specific binding of molecules to a matrix). Additionally or alternatively 'pre-treatment' can involve the changing of physical and/or biochemical properties of molecules in a sample. A "pre-treatment region" when referring to a device is a region in a device conceived to ensure pre-treatment of a sample.

An "aggregation factor" as used herein, refers to one or more substances that induce aggregation of molecules. The aggregation can be aggregation of the aggregation factor itself, aggregation of an analyte to be detected, aggregation of assay molecules (e.g. antibodies or particles e.g. magnetizable particles) used in the detection process, or aggregation of any other substance present in the sample or used during the detection of the analyte. Typically, aggregation caused by an aggregation factor results in decreased efficiency or accuracy of detection of the analyte. Saliva is known to contain different aggregation factors (see e.g. Van Nieuw Amerongen et al., Bohn Stafleu Van Loghum (Houten, The Netherlands), 2004), and these aggregation factors form part of the fraction of the saliva sample that may interfere with detection of one or more analytes. Typical examples of aggregation factors in saliva include S-IgA, mucins, high-molecular glycoproteins such as agglutinin, proline-rich glycoprotein (PRG), and lysozyme.

The term "detection region", when referring to a device herein refers to a region within the device where detection of the presence of the analyte in the sample occurs by ways of a detector capable of recording a signal generated within the detection region.

The term "biosensor surface" as used herein, refers to a region within the detection region of a device or cartridge where detection is ensured by a detection means. The biosensor surface comprises a biological component and a detector component.

The term "magnetizable particles" as used herein refers to particles or beads that are magnetic in the presence of a(n externally applied) magnetic field and can be manipulated by an externally applied magnetic field, but that do not retain magnetization in the absence of such magnetic field. This includes paramagnetic particles or superparamagnetic particles. Very small magnetic particles (e.g. in the order of 1-20 nm diameter) will lose their magnetization very fast due to thermal effects. In the context of the invention, these particles may also be considered magnetizable particles, equivalent to paramagnetic particles.

The present invention provides devices and methods for detecting the presence of one or more analytes in a sample, in particular a saliva sample. According to a particular aspect, the devices comprise one or more pre-treatment regions for specifically or non-specifically removing at least a part of the fraction of the saliva sample interfering with detection of the one or more analytes; and linked thereto, a detection region.

The one or more pre-treatment regions in the device and methods of the present invention are particularly aimed at increasing sensitivity of detection of potential analytes present in saliva, in the detection region. A number of the substances found in saliva may interfere with detection of analytes. The devices and methods of the invention allow for pre-treatment of the sample, to remove at least part of the substances that may interfere with detection of the analyte. According to particular embodiments, pre-treatment of the saliva sample entails the removal of aggregation factors. Aggregation factors are indeed part of the fraction of the saliva sample interfering with detection of the one or more analytes. According to particular embodiments, the aggregation factor is selected from the group consisting of S-IgA, mucins, high-molecular glycoproteins such as agglutinin, proline-rich glycoprotein (PRG), and lysozyme. According to other particular embodiments, the aggregation factor is (or the aggregation factors are) a mucopolysaccharide, a glycoprotein or a combination thereof. According to further particular embodiments, the aggregation factor is a mucin or a combination of mucins.

Methods and devices of the present invention are of particular interest for the detection of analytes in mucin-containing samples such as saliva samples.

The one or more pre-treatment regions envisaged in the context of the present invention are envisaged to ensure pre-treatment of the sample in one or more different ways. In particular embodiments the one or more pre-treatment regions ensure the removal of at least part of the fraction of the saliva sample that interferes with detection.

In particular embodiments, removal of molecules which interfere with detection is ensured by specifically or non-specifically immobilizing these molecules, while the remainder of the sample (including the analyte) is maintained in the mobile phase. Accordingly, the one or more pre-treatment regions comprise a molecule that binds to the interfering fraction present in saliva but has no or negligible affinity for the analyte to be detected.

In particular embodiments pre-treatment regions are used which comprise materials and/or molecules which bind at least part of the fraction of the saliva sample, or one or more molecules therein, which interfere with detection. In further particular embodiments molecules are used which bind aggregation factors present in saliva.

Examples of materials envisaged in the context of the present invention for use in pre-treatment include, but are not limited to, hydroxyapatite, metal oxides, metal hydroxides (in particular negatively charged metal hydroxides), aluminum hydroxide, metals (such as titanium, iron), polymers (such as, but not limited to, polyethylene derivatives such as polyethylene oxide; polymethylmethacrylate and the like). Hydroxyapatite (HAP) is the major constituent of tooth enamel. This non-toxic material is known to have a certain affinity for different constituents of saliva. In particular, salivary mucins attach to hydroxyapatite. Also, bacteria (e.g. *Streptococcus* species) are known to adsorb to hydroxyapatite. According to specific embodiments, the one or more pre-treatment regions envisaged in the methods and devices of the invention comprise hydroxyapatite. In further particular embodiments, the pre-treatment region(s) comprise(s) a hydroxyapatite filter. In alternative particular embodiments, the pre-treatment region(s) comprise(s) both a filter (in particular a hydroxyapatite-free filter) and hydroxyapatite, for subsequent filtering en hydroxyapatite treatment of the sample.

In particular embodiments of the methods and devices of the invention, specific removal of at least a part of the fraction of the saliva sample interfering with analyte detection is envisaged. In particular embodiments, molecules are used which have a specific affinity for an interfering substance in the saliva. In further particular embodiments the molecules present in the one or more pre-treatment regions capable of specifically binding one or more compounds interfering with the detection of analytes in saliva are molecules which can capture compounds based on a specific biochemical interaction. Typical specific interactions include, but are not limited to DNA/DNA or DNA/RNA binding, protein/protein, protein/DNA and protein/carbohydrate interactions, antibody/antigen interactions, and receptor/ligand binding.

Also synthetic molecules can be used to bind an interfering compound (e.g. modified enzyme inhibitors, small molecules).

According to particular embodiments, the molecules used in the one or more pre-treatment regions which have a specific affinity for one or more interfering substances in the saliva are antibodies. Suitable antibodies include polyclonal and monoclonal antibodies, nanobodies, and fragments or derivatives of such antibodies capable of binding to the antigen against which the corresponding antibody was raised. Antibody fragments include but are not limited to single-chain variable fragments (scFvs), Fab, Fab', F(ab')$_2$, Fv fragments or smaller fragments such as complementarity determining regions (CDR, e.g. CDR1, CDR2 and CDR3) of the heavy or light chain and/or combinations of two or more thereof and other derivatives thereof. According to further particular embodiments, the antibodies are anti-mucin antibodies.

Additionally or alternatively the molecules interfering with analyte detection are removed based on physical properties. For instance, where the analyte is a small molecule, the physical removal of larger molecules or components (e.g. cells) interfering with detection is ensured by filtering. Different biochemical and physical methods may be combined in the one or more pre-treatment regions of devices and methods of the invention. In a particular embodiment, the sample e.g. is first filtered in a non-specific way, and afterwards components are removed specifically (e.g. using antibodies). Thus, in particular embodiments pre-treatment of the sample may comprise more than one pre-treatment step and/or the movement of the sample across or through more than one pre-treatment region. When separate subsequent pre-treatment regions are provided, it is possible to ensure a more complete removal of the interfering fraction.

In further particular embodiments, the one or more pre-treatment regions are regions wherein the sample is contacted with one or more compounds or conditions capable of changing the physical and/or biochemical nature of interfering molecules, such as compounds which neutralize certain components of saliva or compounds or conditions which decrease viscosity (e.g. heat treatment, enzymatic treatment).

The one or more pre-treatment regions envisaged in methods and devices of the invention can take several forms, depending on how the pre-treatment step(s) is/are to be performed. According to particular embodiments, the one or more pre-treatment regions are comprised within one or more chambers of a device which are optionally physically separated from the detection region. In further particular embodiments, the one or more pre-treatment regions are present in a chamber containing magnetizable particles coated with one or more molecules capable of specifically or non-specifically binding to components in the saliva sample interfering with detection. When a saliva sample is introduced into such one or more pre-treatment chambers, the interfering components present in the saliva sample bind to the molecules on the magnetizable particles. Application of a magnetic field can ensure removal of (at least part of) the fraction interfering with detection bound on the magnetizable particles. Where multiple chambers are used, the pre-treated sample is moved from one pre-treatment chamber to the next to ensure optimal removal of interfering factors. The magnetizable particles used to remove interfering components will not be used in detection of the analyte(s).

In alternative embodiments, the one or more pre-treatment regions comprise a surface with a molecule capable of specifically or non-specifically binding to components in the saliva sample interfering with detection of the one or more analytes to be detected.

According to a further particular embodiment, one or more of the one or more pre-treatment regions has a surface, e.g. a sample pad, with molecules specifically binding to components in the saliva sample interfering with analyte detection coated thereon. According to a specific embodiment, these molecules specifically binding interfering components are antibodies, or fragments or derivatives thereof. According to yet a further specific embodiment, the antibodies (or fragments or derivatives thereof) are anti-mucin antibodies.

According to particular embodiments, one or more of the one or more pre-treatment regions comprises a surface to which molecules are bound which bind non-specifically to components in the saliva sample interfering with analyte detection. According to a further specific embodiments, one or more pre-treatment regions comprises a surface to which hydroxyapatite is bound. Additionally or alternatively, one or more pre-treatment regions comprise a surface to which a metal oxide or hydroxide, such as aluminum hydroxide is bound.

The term 'bound' as used in this context should not be interpreted in a restrictive way. Indeed, the format of the materials that bind non-specifically to components in the saliva sample interfering with analyte detection (such as hydroxyapatite) may vary considerably. They can be provided e.g. as a powder, impregnated into or onto a suitable carrier or even be a porous structure made by sintering. Thus, the surface in the one or more pre-treatment regions to which molecules are bound which bind non-specifically to components in the saliva sample interfering with analyte detection, may also be made largely, essentially entirely or entirely out of the molecules that bind non-specifically to components in the saliva sample. According to a particular embodiment, at least part of the surface in the pre-treatment region is a porous sintered structure composed of molecules which bind non-specifically to components in the saliva sample interfering with analyte detection. Alternatively, the molecules that bind non-specifically to components in the saliva sample are provided as a powder where the sample can flow through, so that the powder forms the surface of the pre-treatment region. Thus, the molecules that bind non-specifically to components in the saliva sample may be bound to the surface as well as be part of the surface.

The surface present in the one or more pre-treatment regions may be porous, so that the sample may flow through it, or may be non-porous, allowing the sample to move over it. According to a particular embodiment, a porous surface has pores sufficiently large in order to decrease the eventual pressure needed to speed up the flow of the sample through the porous surface. According to a further particular embodiment, the pore size of the porous surface is at least 200 nm, more in particular at least 500 nm. According to a further embodiment, the pores are on a micrometer scale (i.e. between 1-1000 µm). Thus, in pre-treating the saliva sample, adsorption of interfering components (such as aggregation factors) to the pre-treatment surface may be combined with size exclusion based on the size of the pores. Indeed, aggregation factors such as mucins often form large aggregates which can not pass through the pores.

As indicated above, the devices and methods of the invention are particularly suited for the detection of analytes in saliva or other samples containing interfering fractions.

In methods and devices of the present invention, the saliva sample is typically applied to a pre-treatment region of the device or a region connected directly therewith. It can be applied either in pure form or after undergoing one or more manipulation steps. According to particular embodiments methods and devices of the invention comprise a further manipulation step and/or a sample manipulation area. Manipulations envisaged to be performed on a sample prior to applying it to the (first or only) pre-treatment region include, but are not limited to, dilution of the saliva sample (with water or with a specific buffer), filtering the saliva sample (in particular non-specifically filtering the sample, or non-specifically or specifically filtering the sample in a way non-identical to the pre-treatment envisaged in the pre-treatment region). However, according to specific embodiments it is envisaged to provide rapid and simple methods, and the saliva sample is applied to a region which corresponds to a pre-treatment region as described herein or is directed to such a region without undergoing prior manipulations.

The sample that is applied to the device may be applied directly in fluid form (e.g. as a spit sample, or via pipetting of saliva) or may be applied indirectly from an adsorbent solid medium (e.g. a cotton swab). Adsorbent media suitable for adsorbing saliva are known in the art. Exemplary media that may be used include, but are not limited to, gel, foam, fiber glass, cotton, cellulose, rayon and other synthetic materials. According to particular embodiments, the methods and devices of the invention encompass means to apply the saliva sample directly to the pre-treatment region.

The methods and devices of the invention further make use of a detection region, where detection of the one or more analytes of interest is ensured.

In particular embodiments the methods and devices make use of a biosensor surface in the detection region. The biosensor surface comprises molecules which ensure detection of one or more analytes. The nature of these molecules is determined by the principle on which detection is based. Assay methods for the one or more analytes in the detection region according to the present invention include direct (non-competitive) and competitive assays. According to particular embodiments, the analyte is detected directly. According to alternative particular embodiments, the analyte is detected indirectly. In both types of assays detection can measure either bound or unbound analyte or antigen-specific molecules.

Where direct detection is envisaged, the biosensor surface comprises analyte-specific molecules, i.e. molecules capable of specifically binding the one or more analytes. Where competitive, i.e. indirect detection is envisaged, the biosensor surface comprises analyte or an analyte analogue.

Suitable molecules capable of specifically binding one or more analytes for use in the context of the present invention are essentially of the same nature as the molecules that may be used for specific removal of components interfering with detection, albeit that the analyte-specific molecules interact specifically with the analyte. Typical specific interactions include DNA/DNA or DNA/RNA binding, protein/protein, protein/DNA and protein/carbohydrate interactions, antibody/antigen interactions, and receptor/ligand binding. Also synthetic molecules can be used to detect an analyte (e.g. enzyme inhibitors, pharmaceutical compounds, lead compounds isolated from library screenings). Accordingly, examples of analyte-specific probes include but are not limited to oligonucleotides, antibodies, enzyme substrates, receptor ligands, lectins etc.

According to particular embodiments, the analyte-specific molecules are monoclonal or polyclonal antibodies, nanobodies or fragments or derivatives thereof (as described herein above).

Typically, the analyte-specific molecules are provided on a surface (biosensor surface), whereby binding of the analyte to the analyte-specific molecule can be detected directly or indirectly by the detector. Alternatively, the detection region is provided with a means for contacting the sample with an analyte specific molecule. The binding of the analyte with the analyte-specific molecule can be detected by capturing the complex on a surface (e.g. using a molecule capable of binding the analyte-specific molecules). Additionally or alternatively, the complex is detected in the detection region as a result of a label present on the analyte-specific molecule.

The analytes or analyte-specific probes may be coated directly or indirectly on the biosensor surface. Methods for coating a surface with a biological molecule are known in the art and examples are described herein below.

Detection in the context of the present invention is typically ensured by the presence of a label. Typical labels include, but are not limited to, chromophoric groups, radioactive labels, electroluminescent, chemiluminescent, phosphorescent, fluorescent or reflecting labels.

According to a particular aspect of the methods and devices, detection involves magnetic actuation (which typically involves the use of magnetizable particles). This magnetic actuation may be used for locally concentrating the molecules to be detected, thereby facilitating detection, and/or may be used for the actual detection process, by measuring changes in the magnetic field. For instance, the presence of components (such as particles) can be sensed by e.g. a magnetic sensor element close to the surface and embedded into the material whereof the surface is the outer part. Alternatively, optical detection of particles using FTIR (Fourier transform infrared spectroscopy) can be envisaged, whereby the material, whereof the surface is the outer part, is transparent for the electromagnetic radiation (such as light). Typically, such methods using magnetic detection or optical detection of magnetizable particles can sense components close the surface or being bound to the surface (typically in the order of 10-5000 nanometer).

Thus, in particular embodiments of devices and methods of the invention, the use of magnetic or magnetizable particles is envisaged. Most particularly, detection involves determining the presence and/or quantity of magnetizable particles in the detection region. The magnetizable particles used in the detection region may be different from the magnetizable particles that can be used in the pre-treatment region.

The nature of the magnetizable particle used in the context of the present invention is not critical. Suitable magnetizable particles include completely inorganic particles and particles which are a mixture of an inorganic and an organic material (e.g. a polymer).

Magnetizable particles, in particular paramagnetic and superparamagnetic particles are widely used in biological analysis, e.g. in high-throughput clinical immunoassay instruments, sample purification, cell extraction, etc. Several diagnostic companies (Roche, Bayer, Johnson & Johnson, Abbott, BioMerieux, etc.) fabricate and sell reagents with magnetizable particles, e.g. for immunoassays, nucleic-acid extraction, and sample purification.

Attachment of analyte-specific molecules or analytes to the surface of magnetizable particles can be performed by methods described in the art. For instance, the particles may carry functional groups such as hydroxyl, carboxyl, aldehyde or amino groups. These may in general be provided, for example, by treating uncoated monodisperse, superparamagnetic particles, to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings. Other coated particles may be prepared by modification of the particles according to the U.S. Pat. Nos. 4,336,173, 4,459,378 and 4,654,267. In the case of a particular type of particle, the surface carries-OH groups connected to the polymeric backbone through $(CH_2CH_2O)_{8-10}$ linkages. Other particular particles carry —COOH groups obtained through polymerization of methacrylic acid. For example, the $NH_2$ groups initially present in the particles may be reacted with a diepoxide as described in U.S. Pat. No. 4,654,267 followed by reaction with methacrylic acid to provide a terminal vinyl grouping. Solution copolymerization with methacrylic acid yields a polymeric coating carrying terminal carboxyl groups. Similarly, amino groups can be introduced by reacting a diamine with the above product of the reaction with a diepoxide, while reaction with a hydroxylamine such as aminoglycerol introduces hydroxy groups. The coupling of a bioactive molecule to a particle can be irreversible but can also be reversible by the use of a linker molecule for the crosslinking between particle and bioactive molecule. Examples of such linkers include peptides with a certain proteolytic recognition site, oligonucleotide sequences with a recognition site for a certain restriction enzyme, or chemical reversible crosslinking groups as those comprising a reducible disulfide group. A variety of reversible crosslinking groups can be obtained from Pierce Biotechnology Inc. (Rockford, Ill., USA). Alternatively immobilization of molecules is not carried out by covalent coupling but by physical adsorption, e.g. many, proteins can be easily immobilized onto a surface of hydrophobic nature. This applies to both particle surfaces as well as for immobilizing molecules on a macroscopic surface (e.g. the biosensor surface).

Magnetizable particles are commercially available in various sizes, ranging from nanometers to micrometers. Magnetizable particles of different sizes (such as but not limited to sizes of 10 nm to 5 μm, typically between 50 nm and 1 μm) are envisaged to be suitable for use in the context of the invention, provided that they can be moved by the magnetic field and (optionally) allow sensitive detection. Similarly, the shape of the particles (spheres, spheroids, rods) is not critical. It is envisaged that different types of magnetizable particles, e.g. with different magnetic and/or optical properties can be used simultaneously within one reaction chamber (magnetic particle multiplexing). This may be the case when more than one analyte needs to be detected.

Specific embodiments of methods, devices and tools provided in the present invention envisage the detection of magnetizable particles in a detection region based on their magnetic/magnetizable properties or optical properties. Additionally or alternatively it is envisaged that magnetizable particles can be detected based on the presence of a label either directly attached to the magnetizable particle or indirectly bound to the particle through an analyte. Suitable labels for binding to a magnetizable particle are described hereinabove. Accordingly, in particular embodiments, the magnetizable particle used in methods and devices described herein is labeled. Labels can be attached to magnetizable particles via the inorganic or via the organic component at the outside or can be incorporated into the particle.

In further particular embodiments, molecules (e.g. analyte-specific compounds or analytes) are used which comprise both a magnetizable particle as a label and a non-magnetic label.

As different types of detection are envisaged, the detection region may take different physical forms, depending on the device and on how the detection is performed, and may e.g. be two-dimensional or three-dimensional. The biosensor surface may be porous, so that the sample may flow through it, or may be non-porous, allowing the sample to move over it.

Typically, the nature of the detection region is ensured by a detector i.e. a detection means can detect the presence on the analyte in the detection region, e.g. on the biosensor surface. In particular embodiments, detection is based on a signal such as but not limited to a magnetic signal, magnetoresistance, a Hall effect, an optic signal (reflection, absorption, scattering, fluorescence, chemiluminescence, RAMAN, FTIR, etc.), an acoustical signal (quartz crystal microbalance (QCM), surface acoustic waves (SAW), Bulk Acoustic Wave (BAW) etc.). In most particular embodiments, the signal is an optical signal, such as a color change which can be detected without specialized equipment. The generation of the signal may be direct, i.e. a direct effect of the label which is bound to the surface or may be the result of the adding of a reactive agent, e.g. the substrate of an enzyme which ensures a color change.

A particular aspect of the present invention relates to devices comprising one or more pre-treatment regions for specifically or non-specifically removing at least a part of the fraction of the saliva sample interfering with detection of the one or more analytes and a detection region, which allows detection of one or more analytes.

According to particular embodiments, the (last or only) pretreatment region and the detection region are immediately adjacent to each other. Alternatively, the pre-treatment region and detection region are separated by an inert region, channel or chamber. Typical examples of such inert regions include, but are not limited to, microfluidic channels in a microfluidics device (see FIG. 1), solid substrates (possibly with capillary action) in a lateral flow device, and so on.

The movement from one pre-treatment region to another and/or from a pre-treatment region, optionally through an inert region, to the detection region can be ensured in different ways. In particular embodiments, the sample flows vertically through a device comprising one or more pre-treatment regions and a detection region. This can be based either on gravitational force or on capillary attraction. Additionally or alternatively, the device is conceived to ensure lateral flow, e.g. by capillary forces or a force generating a fluid current in the device (e.g. by mechanical fluid flow or acoustic or ultrasonic fluid excitation). In particular embodiments, physical attributes of the device ensure movement of the particles towards a pre-treatment and/or detection region e.g. funnel-shaped towards the binding surface.

In particular embodiments, devices are provided which make use of magnetic particles which are moved in a magnetic field. Most particularly, the use of magnetic/magnetizable particles is envisaged in the detection region. Additionally or alternatively, the use of magnetizable particles is envisaged in the one or more pre-treatment regions. The force exerted on a magnetic (or magnetizable) particle by a magnetic field is given by the gradient of this field and the magnetic susceptibility of the particle. The magnetic force can be calculated (see for example J. D. Jackson, Classical Electrodynamics, John Wiley & Sons, Inc., 1999). As a result, the force on a magnetic particle relates to the gradient of the magnetic field. In other words, a magnetic particle has a tendency to move from a region of lower to a region of higher magnitude of the magnetic field.

In the case where magnetic actuation is envisaged both in the pre-treatment and the detection regions, the magnetic actuation is not performed simultaneously in the different regions, but subsequent to each other, as the sample is moved from one region to the next.

Accordingly, systems are provided wherein one or more magnetic fields can be generated by one or more magnetic field generating means. Different types of magnetic field generating means are envisaged in the context of the present invention, such as permanent magnets, electromagnets, coils and/or wires. The strength of the magnetic force on the particles is such that the induced travel distance is larger than the distance travelled without magnetic fields, i.e. the magnetic forces should be dominant over translational Brownian motion.

According to the present invention, magnetic field(s) generated by the one or more magnetic field generating means can be constant, pulsating, or can vary in strength. Moreover, where more than one magnetic field is generated, their exact orientation may be fixed or may vary.

According to particular embodiments, the magnetic field generating means comprises an electromagnet or one or more electric wires. This makes it possible to avoid mechanical moving of parts in the device. According to particular embodiments, a magnetic field generating means is placed below the pre-treatment region(s) and/or the detection region.

In particular embodiments of the methods and devices described herein, at least one magnetic field ensures the movement towards a region within the detection region which is the biosensor surface where detection occurs. Devices are envisaged which are cartridges which can be used in combination with a means for generating a magnetic field. Additionally or alternatively the means for generating a magnetic field is incorporated into the device.

According to specific embodiments, devices are provided which do not rely on the application of an external physical force (e.g. the application of pressure by a plunger).

In particular embodiments, devices according to the present invention, are lateral flow devices. In further particular embodiments the devices are microfluidic devices or (disposable) cartridges for use in a microfluidic device. A microfluidic device as used herein refers to a device which has features (such as channels) whereof at least in one dimension the size is in the range of 0.05 to 5000 micrometer, more in particular between 10 and 500 micrometer.

According to particular embodiments, the devices of the present invention comprise one or more pre-treatment regions comprising hydroxyapatite.

The devices of the present invention further comprise a detection region. In particular embodiments, the detection region comprises a biosensor surface/This is typically a specially derivatized surface to which molecules, more particularly probes can be bound. Examples of suitable surfaces include, glass, metal, plastic, an organic crystal or an inorganic crystal (e.g. silicon), an amorphous organic or an amorphous inorganic material (e.g. silicon nitride, silicon oxide, silicon oxinitride, aluminum oxide). Suitable surface materials and linking chemistries are known to the person skilled in the art, and are described for instance in "Diagnostic Biosensor Polymers", by A. M. Usmani and N. Akmal, American Chemical Society, 1994 Symposium Book Series 556, Washington D.C., USA, 1994, in "Protein Architecture, Interfacing Molecular Assemblies and Immobilization Biotechnology", edited by Y. Lvov and H. Mhwald (Marcel Dekker, New York, 2000), in "The Immunoassay Handbook" by David Wild (Nature Publishing Group, London, 2001, ISBN 1-56159-270-6) or "Handbook of Biosensors and Electronic Noses. Medicine, Food and the Environment" by Kress-Rogers (ISBN 0-8493-8905-4). Supports for coupling proteins to coated and uncoated plastic and glass supports are disclosed in Angenendt et al. (2002; *Anal Biochem.* 309, 253-260). Dufva (2005; *Biomol Eng* 22, 173-184), review the methodology to attach oligonucleotides and factors influencing this process.

In particular embodiments, systems and devices are provided wherein the biosensor surface is coated by an analyte, analyte-analogue or analyte-specific probe.

Devices according to the invention may be provided as cartridges for use in combination with a detection means which ensures detection of the analyte in the detection region. Additionally or alternatively, suitable detection means may be incorporated into systems and devices for performing methods described herein. Suitable detection means include means capable of detecting the relevant signal such as, but not limited to a magnetic signal, magnetoresistance, a Hall effect, an optic signal (reflection, absorption, scattering, fluorescence, chemiluminescence, RAMAN, FTIR, etc.), an acoustical signal (quartz crystal microbalance (QCM), surface acoustic waves (SAW), Bulk Acoustic Wave (BAW) etc.). In particular embodiments, a detection means is provided which is a magnetoresistance element.

Thus, according to particular embodiments, a sensor for detecting magnetic particles in or on the biosensor surface is integrated into the detection region (e.g. magnetoresistive sensor is integrated). Alternatively, the detection means or sensor (e.g. optical unit) is not an integrated part of the device. In these embodiments, the detection region optionally comprises a detection window, which allows the detection of a label in the detection region, more particularly on the biosensor surface. The location of the detection window is determined by the location of the biosensor surface within the detection region. Most particularly, the detection window is centrally located as a spot or longitudinal region above or below the biosensor surface, corresponding with the biosensor surface.

In particular embodiments, detection is ensured by a sensor below the biosensor surface in the detection region. Optionally, a detection window is provided in the material supporting the biosensor surface.

Where the detection is based on magnetic field or optical methods, the provision of a specific detection window may be superfluous, e.g. where all or part of the detection region and/or biosensor surface material is transparent for the signal to be detected.

Further particular embodiments of systems and devices described herein comprise, in addition to the components described above, one or more of the following components. The system of the invention will usually comprise one or more inlet means for introducing sample, magnetizable particles and/or reagents into the reaction chamber. These can optionally be coupled to sources comprising each of the reagents. Optionally, devices according to the invention comprise an outlet means for removing reagents, reaction waste, and/or optionally, magnetizable particles, from the biosensor surface and/or detection region.

Particular embodiments of the present invention provide (optionally disposable) cartridges integrating the pre-treatment and detection regions described herein. Disposable cartridges can further comprise magnetizable particles integrated therein or these can be provided separately. In particular embodiments, the material of the cartridge is such that magnetic fields can be generated therein. For example, the cartridge is made of glass or a synthetic material, such as plexiglass [poly(methy)methacrylate] or clear PVC (polyvinyl chloride) or PC (polycarbonate) or COP (e.g. Zeonex) or PS (polystyrene).

Cartridges envisaged in the context of the present invention further optionally comprise at least one physical carrier for generating a magnetic field gradient.

The devices described in the present invention can be used as rapid, robust, and easy to use point-of-care biosensors for small sample volumes. As detailed above, the device or cartridge can be a disposable item to be used with a compact reader, optionally containing one or more magnetic field generating means and/or one or more detection means. Optionally, only one or more parts of the device are disposable (e.g. the pre-treatment region(s), the detection region, or just the biosensor surface).

According to yet a further aspect, the invention provides methods whereby the devices and/or cartridges of the present invention are used for the detection and/or quantification of analytes in a saliva sample.

The nature of the analyte to be detected is not essential to the invention. Methods envisaged in the context of the present invention include the detection of analytes which are different types of molecules, more particularly biomolecules such as DNA, RNA, proteins, carbohydrates, lipids and organic anabolites or metabolites. However, according to a particular embodiment, methods are provided to detect the presence of drugs in a saliva sample.

Methods to detect drugs in fluid samples are well known in the art, and e.g. described in WO 02/082040. Drugs that can be tested using the methods of the invention include, but are not limited to, psychedelic agents, psychostimulants, sedatives, depressants, abused inhalants, hypnotics and alcohol. According to a particular embodiment, the one or more analytes to be detected are one or more drugs selected from the group of alcohol, opiates (OPI), cocaine (COC), cannabinoids such as cannabis or in particular tetrahydrocannabinol (THC), amphetamines/metamphetamines (AMP), Morphine (MOR), Benzodiazepines (BZO), 1-(1'-phenylcyclohexyl) piperidine (PCP), Barbiturates (BAR), Methadone (MET) and heroin or other opioids with a morphine-like action, such as, but not limited to, codeine, papaverine, noscapine, hydrocodone, or fentanyl. Derivatives or metabolites of these drugs may also be detected. According to specific embodiments, the methods are particularly suitable for drug of abuse testing.

Different assay principles are envisaged in the detection methods of the invention.

In particular embodiments, detection is based on direct detection of the analyte by the binding to an analyte-specific probe.

Figure 2A:
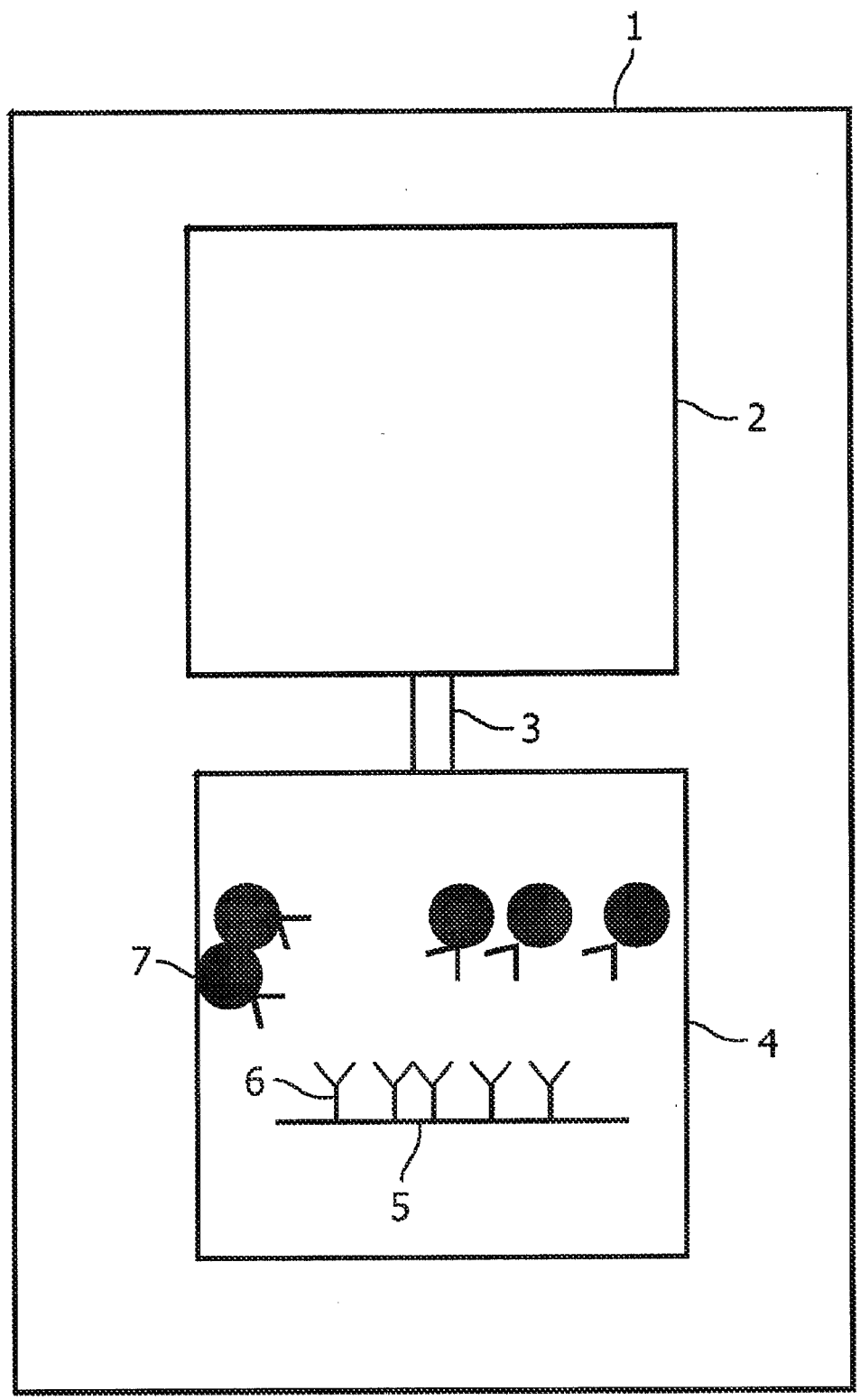
FIG. 2 shows a schematic representation of a device (1) according to a particular embodiment of the invention, comprising a pre-treatment region (2) and detection region (4). The detection region (4) comprises a biosensor surface (5) which comprises, in this embodiment, molecules (6) capable of specifically binding the one or more analytes. In the specific embodiment shown here, the device comprises means for contacting the detection region (4) with magnetizable particles (7) coated with a molecule capable of specifically binding the one or more analytes. In particular embodiments of the use of device (1), a saliva sample is applied on the pre-treatment region (2) which comprises molecules that specifically or non-specifically remove at least a part of the fraction of the saliva sample interfering with detection of the one or more analytes. The pre-treated sample then is transported to the detection region (4), in this particular embodiment through a microfluidics channel (3). The analytes (8) present in the sample are allowed to bind to the molecules (6) capable of specifically binding the analytes comprised on the biosensor surface (5). Application of a magnetic field causes the movement of unbound magnetizable particles (7) towards the biosensor surface (5) where they can bind to the analytes (8) present. After a predetermined time, the magnetic attraction field is removed. Another magnetic field is applied to pull the non-bound magnetizable beads away from the biosensor surface (5). The presence of the labeled magnetizable particles (indicative of the presence of the analyte) on the biosensor surface is then detected by appropriate detection means. A the device prior to use. B: device during detection of analyte in a sample.
Figure 2B:
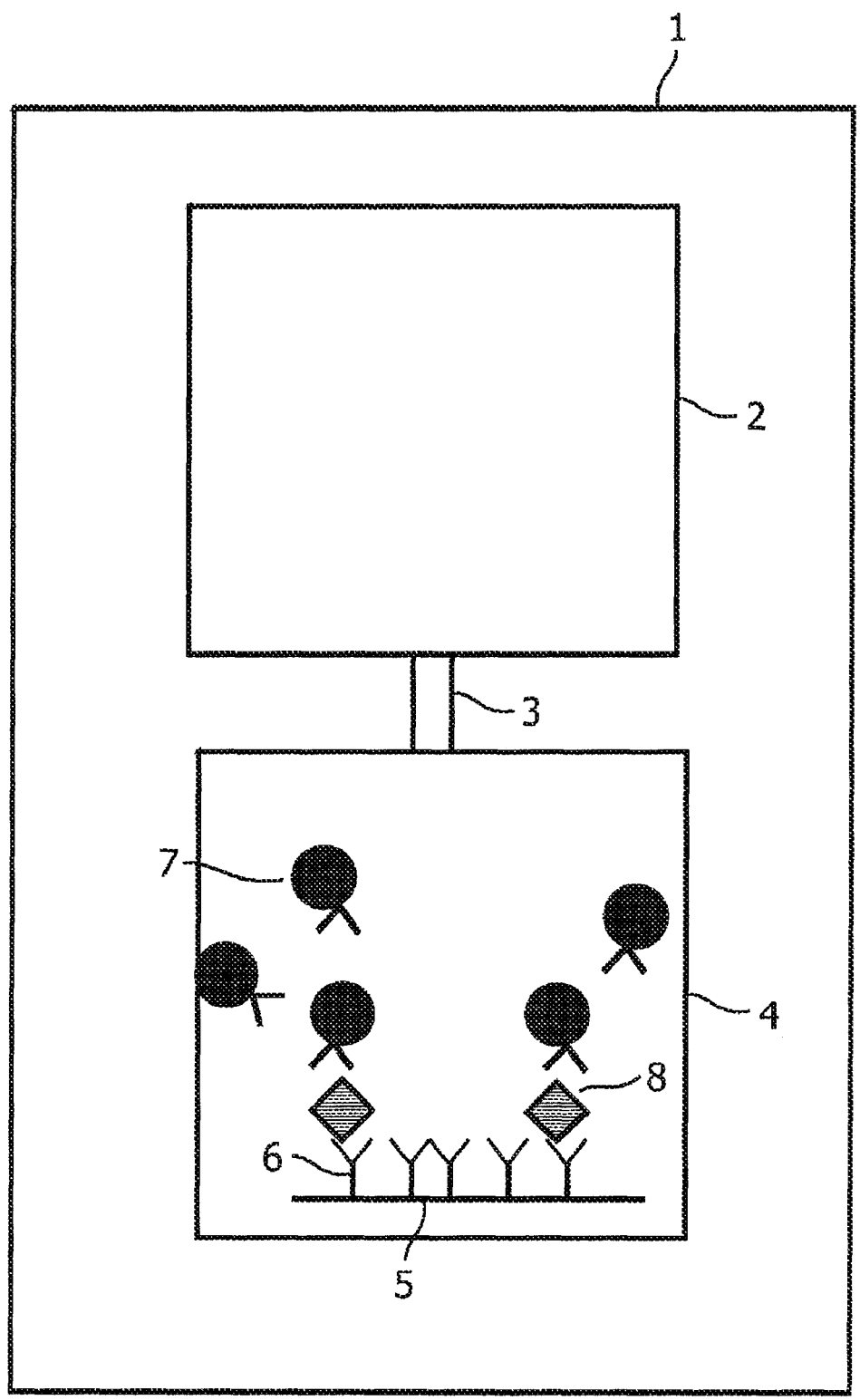

This is illustrated by a particular embodiment in FIGS. 2A and 2B. Herein a device is provided comprising a detection region (4) which comprises analyte-specific probes (6) linked to a biosensor surface (5). In the detection region, the sample is contacted with magnetizable particles (7) coated with a molecule capable of specifically binding to the analyte(s) in the saliva sample to be detected. According to particular embodiments, these molecules are not identical to the molecules on the biosensor surface, to ensure that both molecules can simultaneously bind the analyte of interest. During use of the device illustrated in FIG. 2B, the analytes (8) in the saliva sample bind to the analyte-specific molecules on the magnetizable particles (7). After removal of the unbound magnetic particles from the biosensor surface (5) by the application of a magnetic field, the bound magnetic particles can be detected.

In particular embodiments detection is based on competitive binding of the analyte to an analyte-specific probe. For example, methods are envisaged whereby the biosensor surface is coated with an analyte-like compound or analyte analogue. Analyte-specific probes labeled with magnetizable particles are contacted with the biosensor surface and bind weakly to the analyte-like compound. Upon contacting with a sample comprising the analyte, the analyte binds strongly to the analyte-specific probe, which is displaced from the biosensor surface. The remainder of magnetizable particles (bound to the analyte-specific probe) in the detection region is inversely proportionate with the concentration of analyte in the sample.

In further alternative embodiments of a competitive assay, analyte-specific probes are bound to the binding surface and magnetically labeled analyte-analogue or analyte are added to the sample prior to contacting the sample with the binding surface.

In particular embodiments of methods envisaged herein, detection of the analyte requires the addition to the detection region of one or more further reagents such as secondary antibodies, labels, substrates etc. . .

It will be clear to the skilled person that the above-described embodiments are not limiting to the invention and that further variations on the assays described above are envisaged.

In particular embodiments of the methods described herein, instead of washing away unbound magnetizable particles, unbound magnetizable particles are used to determine the presence (and quantity) of the analyte.

According to particular embodiments, methods of the present invention involve the contacting of sample with magnetizable particles (e.g. magnetically labeled analyte-specific probes or magnetically labeled analyte or analyte-analogue) and the movement of particles within a pretreatment region and/or within a detection region. Magnetizable particles can be part of a fluid reagent or of a dry reagent. Besides magnetizable particles, the reagent can for example contain buffer salts, detergents, biomolecules that assist in the biological interactions, etc. These steps can be performed in a liquid, which is any liquid compatible with the reagents used (i.e. analyte, analyte-specific probe, label), such as standard buffers, or minimally pre-treated or even pure sample (e.g. blood or saliva). Liquid can be introduced in the pre-treatment and/or detection regions for rinsing purposes. Alternatively, the methods are performed with a minimum amount of liquid, particularly at the biosensor surface.

According to particular embodiments, the methods of the present invention further comprise a detection step, which allows determining qualitatively or quantitatively the amount of label present in the detection region, which is a (direct or indirect) measure for the amount of analyte in the sample. The detection step is ensured using one or more detection means as described above.

A further aspect of the invention relates to the use of hydroxyapatite for the pre-treatment of saliva samples in the detection of analytes. Pre-treatment of a saliva sample one or more times with hydroxyapatite removes mucin molecules from the sample preventing their interference with the mobility of the sample and in the detection of the analyte.

Accordingly, the present invention provides methods for determining an analyte in saliva, which methods comprise contacting the saliva sample at least once with hydroxyapatite. In particular embodiments the hydroxyapatite pre-treatment is combined with a filtering step.

In particular embodiments of this aspect of the invention, the pre-treatment with hydroxyapatite is integrated in a detection device or cartridge.

In particular embodiments of this aspect of the invention devices are provided which comprise, in addition to a detection region, a hydroxy-apatite loaded filter.

In particular embodiments, magnetizable particles are used in the detection of the analyte. More particularly, the magnetic properties of the magnetizable particles are used to detect the presence and or quantity of magnetizable particles accumulated in the detection region. In addition or alternatively, the detection of magnetizable particles is performed visually or optically based on optical properties of the particle or of labels which are attached directly or indirectly to the magnetizable particles (see above). According to a particular embodiment, FTIR spectroscopy is used for the detection of the analyte when using magnetizable particles.

Other arrangements for embodying the invention will be obvious for those skilled in the art. It is to be understood that although preferred embodiments, specific constructions and configurations, as well as materials, have been discussed herein for devices and methods according to the present invention, various changes or modifications in form and detail may be made without departing from the scope and spirit of this invention. The invention is illustrated by the Examples provided below which are to be considered for illustrative purposes only and the invention is not limited to the specific embodiments described therein.

The device and method according to the invention are in particular suitable for carrying out immunoassays, more in particular immunoassays that are carried out as competition assays.

EXAMPLES

Example 1

Removal of Interfering Mucin by Repeating the Pre-Treatment Step

Super paramagnetic beads are coated with a molecule capable of specifically binding an interfering compound of saliva, in this case an anti-mucin antibody. In a first step a saliva sample is contacted with a first pre-treatment region comprising the paramagnetic bead coated with the anti-mucin antibody. By application of a magnetic field the beads are removed from the fluid. The sample is then moved to a second pre-treatment region. The effect of the contacting of the sample with the paramagnetic beads (e.g. the clustering or aggregation status of the superparamagnetic beads caused by the mucins can be monitored during the contacting with the pre-treatment region. This is done by studying the sample, or an aliquot thereof, under a microscope, or for example by using a Nanosizer (Malvern instruments). When aggregation or clustering is observed, the pre-treatment step is repeated (either by applying the sample to a further pre-treatment region or by re-applying the sample to the first pre-treatment region, from which the superparamagnetic particles have been removed and replaced with fresh coated superparamagnetic particles. Optionally, the pre-treatment step is repeated until no more clustering of the beads is observed.

Next, the saliva sample is transferred to a detection region, where detection of the analyte takes place. In this example, the analyte is morphine. Morphine is a small molecule, with only one epitope, so a competitive assay has to be performed to determine the amount of morphine in a sample.

Morphine-BSA conjugate is coated on the polystyrene surface of the detection region by applying 1 µl of BSA-morphine (1 mg/ml in phosphate buffered saline (PBS)) homogeneously on the well and drying it (morphine-3-glucoronide is coupled in excess BSA via its lysine residues). After coating, the surface is blocked with 10 mg/ml BSA+0.65% Tween-20 in PBS for 1 hour. Then, the blocking solution is discarded.

The saliva sample obtained from the (one or more) pre-treatment region is contacted with the surface in the detection region with the coated morphine. At the same time paramagnetic particles coated with anti-morphine antibodies (a 1:10 dilution of anti-morphine Ab coated paramagnetic particles (200 nm Protein G coated magnetic particles) in a solution of 10 mg/ml BSA+0.65% Tween-20 in PBS, total amount of solution is 50 µl) are added. In the absence of morphine in the saliva, all the magnetizable particles with the antibody bind to the morphine coated on the well. To ensure efficient binding, a magnetic field is applied to attract the paramagnetic beads to the sensor surface. When morphine is present in the saliva (or in a control sample, which has been spiked with 1 to 40 ng/ml morphine), a fraction of the antibodies is saturated with morphine of the saliva and does not bind to the analyte coated on the surface.

Upon application of a second magnetic field oriented away from the surface, the magnetizable particles not bound to the coated analyte can be removed from the biosensor surface. Detection is performed by measuring the amount of paramagnetic particles bound to the biosensor surface.

Example 2

Rapid Detection of Amphetamines Using a Lateral Flow Assay

A saliva sample is added to a pre-treatment region comprising a sample pad (a porous structure) with anti-mucin antibodies immobilized onto the surface of the sample pad material. The mucins present in the saliva will bind to the immobilized anti-mucin antibodies. The incubation time can be influenced by the size of the sample pad and/or the pore size of the sample pad. The number of immobilized antibodies and the incubation time with the sample pad is adjusted such that the interfering matrix components are sufficiently removed and therefore the a-specific binding or aggregation/clustering of the mobile solid phase is no longer an issue.

After moving through the pre-treatment zone, the sample transits to a zone where it is contacted with colored particles which are labeled with amphetamine or an amphetamine analogue. The sample then further moves to the detection region, comprising a detection region with anti-amphetamine antibodies placed so as to form a 'detection line'. (Unlabelled) amphetamine present in the saliva sample will take up the binding sites on the labeled anti-amphetamine antibodies, thereby preventing the binding and concentration of the amphetamine labeled with colored particles in the detection line. In the absence of amphetamine in the sample, all of the labeled amphetamine binds in the detection zone, resulting in a colored band. This can be detected visually.

Example 3

Detection of Opiate in Assays Making Use of HAP Filtration

Superparamagnetic particles (Ademtech 500 nm COOH coated particles) were coated with monoclonal anti-opiate antibodies. The detection region is prepared by providing a surface coated with BSA-opiate. The top and bottom part of the biosensor was assembled by using tape, and the sensors were kept under lab conditions at room temperature. Four different pre-treatment conditions were used: no pre-treatment, Sponge Bob filter material (Filtrona, density 0.29 g/cm$^3$), and contacting with 50 mg/ml HAP followed by a filter. Next, the particles were redispersed at 0.2 wt % in the pretreated buffer or saliva.

Samples comprising either assay buffer or 70% saliva (saliva donor 1-3) in assay buffer were subjected to the different pre-treatment regions and subsequently mixed with the magnetizable particles.

The detection of opiates in samples obtained from the different pre-treatment conditions was performed using a competitive assay in an optical biosensor system. No drugs were applied to obtain maximum signal in the competitive assay. The samples were contacted with the detection region by autonomous filling through a capillary channel. A magnetic field was applied attracting the magnetic beads to the biosensor surface. Magnetic attraction/actuation was applied by using a magnetic coil system. Another magnetic field above the cartridge was applied to pull the non-bound beads away from the substrate surface. The total assay time (filling, redispersion and magnetic actuation) was 35 seconds (5 s cartridge filling, 30 s actuation).

Figure 3:
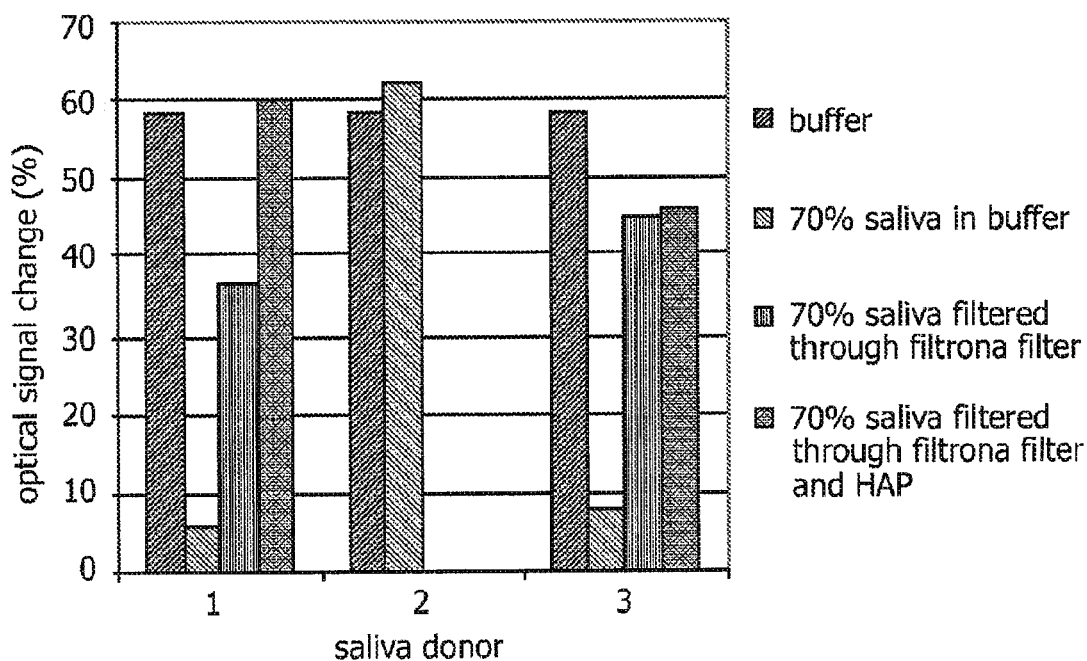
FIG. 3 shows the assay functionality after hydroxyapatite filtering in the pre-treatment region. The analyte of interest is opiate. In this experiment, the biosensor surface was coated with BSA-opiate and detection was performed with superparamagnetic particles coated with anti-opiate antibodies. A competition assay was performed to determine the detectability of opiate in samples without pre-treatment (dilution with 30% buffer), pre-treatment by filtering and pre-treatment by filtering combined with hydroxyapatite-pretreatment. Results are shown for saliva samples from three test persons. % optical signal change refers to change in signal after addition of superparamagnetic particles.

The assay results are summarized in FIG. 3. It can be seen that the results are variable when no hydroxyapatite filtering step is used. Indeed, in sample 2, mere dilution of the sample was enough to yield similar results as buffer with no opiate. However, in samples 1 and 3, from different individuals, the sample matrix interfered with detection. Whereas filtering may overcome this issue for some samples (see e.g. sample 3), it can be observed that filtering in combination with contacting with hydroxyapatite is most appropriate to yield correct results for sample 1. Thus, hydroxyapatite increases sensitivity of the assay.

Similar results can be obtained when using hydroxyapatite (e.g. as a nanopowder) immobilized onto a filter. Such filter can be incorporated into a cartridge of a microfluidics device, so that the sample will flow through this filter before the sample flows into the microfluidics channel and towards the test chamber.

Similar results can also be obtained with magnetizable beads dried onto the top part of the cartridge. Saliva is then first subjected to the pre-treatment region containing the magnetizable particles. Next the samples are contacted with the detection region by autonomous filling through a capillary channel. In the detection region the magnetic particles redisperse and an assay is performed with magnetic actuation as described above (see also Example 4).

Example 4

Competitive Opiate Assay Making Use of HAP Filtration and Dried Beads for Detection Superparamagnetic particles (Ademtech 500 nm COOH coated particles) were coated with monoclonal anti-opiate antibodies. The detection region is prepared by providing a surface coated with BSA-opiate (3 printed spots). Magnetic particles were redispersed in drying buffer (10 mM Tris HCl, 1 wt % BSA, 10 wt % sucrose, pH 7.5) The top and bottom part of the biosensor was assembled by using tape, and the sensors were kept under lab conditions at room temperature. 2 different pre-treatment conditions were used: BNW filter material (Filtrona, density 0.3 g/cm$^3$), and contacting with 20 mg/ml HAP per 500 µl saliva followed by a BNW filter. Samples comprising 100% saliva (saliva donor 1-5) were subjected to the different pre-treatment regions and subsequently guided to the detection chamber.

The competitive assay in samples obtained from the different pre-treatment conditions was performed using an optical biosensor system. No drugs were applied to obtain maximum signal in the competitive assay. The samples were contacted with the detection region by autonomous filling through a capillary channel. A magnetic field was applied attracting the magnetic beads to the biosensor surface. Magnetic attraction/actuation was applied by using a magnetic coil system. Another magnetic field above the cartridge was applied to pull the non-bound beads away from the substrate surface. The total assay time (filling, redispersion and magnetic actuation) was 35 seconds (5 s cartridge filling, 30 s actuation).

Figure 4:
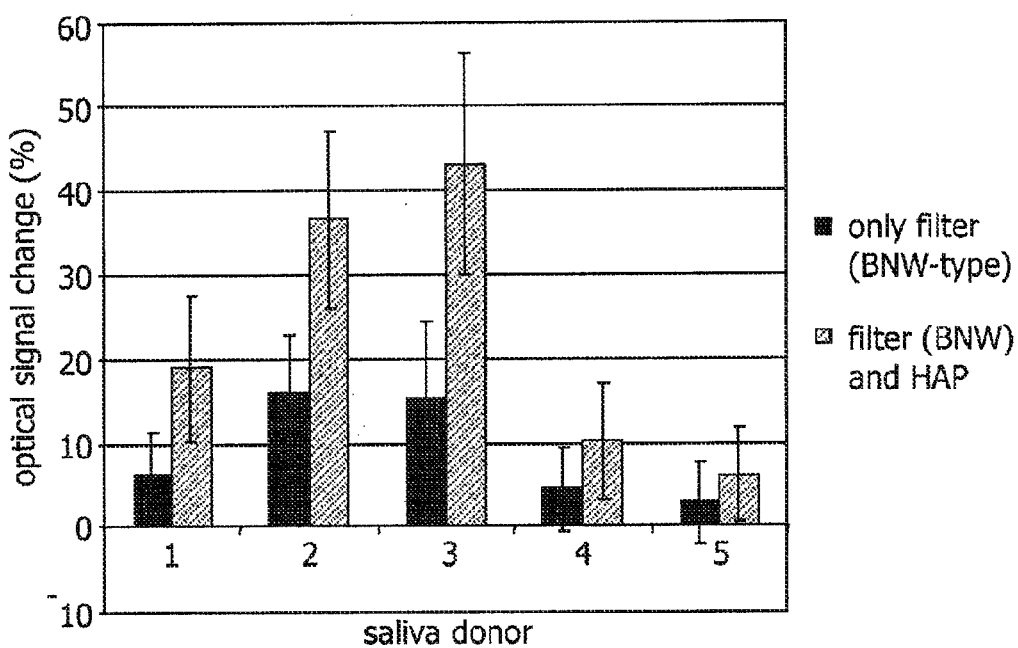
FIG. 4 shows the assay functionality after hydroxyapatite filtering in the pre-treatment region. The analyte of interest is opiate. In this experiment, the biosensor surface was coated with BSA-opiate and detection was performed with superparamagnetic particles coated with monoclonal anti-opiate antibodies. A competition assay was performed to determine the detectability of opiate in samples pre-treated by filtering or pre-treated by hydroxyapatite pre-treatment in combination with filtering. Results are shown for saliva samples from five test persons. % optical signal change refers to change in signal after addition of superparamagnetic particles.

The assay results are summarized in FIG. 4. It can be seen that the results are always lower when no hydroxyapatite filtering step is used (expressed as % signal change after addition of the superparamagnetic beads). These lower signals in the competitive detection assay could be misinterpreted as a positive signal. It can be observed that filtering in combination with contacting with hydroxyapatite is most appropriate to yield high signals for saliva samples. Thus, hydroxyapatite increases sensitivity of the assay and reduces the risk of false positive results.

The invention claimed is:

1. A microfluidic device for detecting the presence of one or more analytes in a saliva sample, comprising:
   (a) one or more pre-treatment chambers comprising a pre-treatment non-porous surface with hydroxyapatite bound as a first molecule capable of specifically or non-specifically binding to one or more saliva components in the saliva sample interfering with the detection of the one or more analytes to thereby specifically or non-specifically remove at least a part of the one or more saliva components in the saliva sample interfering with detection of the one or more analytes; and
   (b) a detection chamber separate from and fluidically coupled to the one or more pre-treatment chambers and comprising a biosensor surface, the biosensor surface comprising:
      second molecules capable of specifically binding the one or more analytes; or
      the one or more analytes and/or second molecules which are structurally related to the analyte and bind analyte-specific probes.

2. The device according to claim 1, the one or more pre-treatment chambers further containing a third molecule being magnetizable particles coated with said first molecule capable of specifically or nonspecifically binding to the one or more components in the saliva sample interfering with detection of the one or more analytes.

3. The device according to claim 1, wherein the hydroxyapatite is porous.

4. The device according to claim 1, wherein the hydroxyapatite has a sintered porous structure.

5. The device according to claim 2, wherein the hydroxyapatite is porous.

6. The device according to claim 2, wherein the hydroxyapatite has a sintered porous structure.

7. The device according to claim 1, which further comprises an intermediary region for containing the saliva sample prior to contacting the sample with the detection chamber.

8. The device according to claim 2, which further comprises an intermediary region for containing the saliva sample prior to contacting the sample with the detection chamber.

9. The device according to claim 4, which further comprises an intermediary region for containing the saliva sample prior to contacting the sample with the detection chamber.

10. The device according to claim 1 wherein the detection chamber containing magnetizable particles coated with the second molecule capable of specifically binding the one or more analytes.

11. The device according to claim 2, wherein the detection chamber containing magnetizable particles coated with the second molecule capable of specifically binding the one or more analytes.

12. The device according to claim 4, wherein the detection chamber containing magnetizable particles coated with the second molecule capable of specifically binding the one or more analytes.

13. The device according to claim 1, wherein the device is a single use device.

14. The device according to claim 1, wherein the one or more saliva components in the saliva sample interfering with the detection of the one or more analytes are selected from the group consisting of mucins, mucopolysaccharides and glycoproteins.

* * * * *